(12) United States Patent
Akita et al.

(10) Patent No.: US 7,416,304 B2
(45) Date of Patent: Aug. 26, 2008

(54) OPHTHALMIC OBSERVATION APPARATUS

(75) Inventors: Junichi Akita, Aichi-ken (JP);
Katsuyasu Mizuno, Gamagori (JP);
Akihiro Fujishiro, Toyohashi (JP)

(73) Assignee: Nidek Co., Ltd., Gamagori-shi (JP)

( * ) Notice: Subject to any disclaimer, the term of this patent is extended or adjusted under 35 U.S.C. 154(b) by 741 days.

(21) Appl. No.: 11/089,205

(22) Filed: Mar. 25, 2005

(65) Prior Publication Data
US 2005/0231685 A1    Oct. 20, 2005

(30) Foreign Application Priority Data
Mar. 31, 2004    (JP)    ............... 2004-101636

(51) Int. Cl.
*A61B 3/10*    (2006.01)
(52) U.S. Cl. ...................... 351/215; 351/214
(58) Field of Classification Search ................. 351/205, 351/206, 213, 214, 215
See application file for complete search history.

(56) References Cited
U.S. PATENT DOCUMENTS
5,177,511 A    1/1993    Feuerstein et al.
5,847,805 A *  12/1998  Kohayakawa et al. ....... 351/210
6,704,106 B2 * 3/2004   Anderson et al. ........... 356/367

FOREIGN PATENT DOCUMENTS
JP    B2 3-51408    8/1991
JP    A 06-114008   4/1994

* cited by examiner

*Primary Examiner*—Huy K Mai
(74) *Attorney, Agent, or Firm*—Oliff & Berridge, PLC

(57)    ABSTRACT

An apparatus for observing an eye of an examinee, comprises: an irradiation optical system for irradiating and two-dimensionally scanning a laser beam onto an observational objective part of the eye; an observation optical system having a photo-receiving element, for photo-receiving the laser beam reflected by the objective part to obtain an image of the objective part, the observation optical system sharing at least a part of the irradiation optical system; a display which displays the obtained image; a polarizing member arranged on an optical axis of the observation optical system, an arrangement angle of the polarizing member with respect to the optical axis being changeable to change a polarized component to be transmitted by the polarizing member.

3 Claims, 3 Drawing Sheets

OPHTHALMIC OBSERVATION APPARATUS

BACKGROUND OF THE INVENTION

1. Field of the Invention

The present invention relates to an ophthalmic observation apparatus for observing an eye of an examinee.

2. Description of Related Art

There is an apparatus constructed to irradiate and scan a laser beam in two dimensions over an objective part to be observed such as a fundus and receives the beam reflected by the objective part by a photo-receiving element (a photo-detector) to produce an image of the objective part. The apparatus of this type includes an apparatus in which the photo-receiving element receives the beam reflected from the objective part through a pinhole placed in a conjugate relationship with respect to the objective part, thus producing a high-resolution image of the objective part. However, the light amount of the beam reflected by the objective part is small. If noise light (scattered light) besides the reflected beam is allowed to pass through the pinhole and is received by the photo-receiving element, the resolution of the objective part image would be reduced, which makes it difficult to observe the objective part.

SUMMARY OF THE INVENTION

The present invention has been made in view of the above circumstances and has an object to overcome the above problems and to provide an ophthalmic observation apparatus with a simple structure and capable of producing a high-resolution image of an objective part to be observed.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the purpose of the invention, there is provided an apparatus for observing an eye of an examinee, comprising: an irradiation optical system for irradiating and two-dimensionally scanning a laser beam onto an observational objective part of the eye; an observation optical system having a photo-receiving element, for photo-receiving the laser beam reflected by the objective part to obtain an image of the objective part, the observation optical system sharing at least a part of the irradiation optical system; a display which displays the obtained image; a polarizing member arranged on an optical axis of the observation optical system, an arrangement angle of the polarizing member with respect to the optical axis being changeable to change a polarized component to be transmitted by the polarizing member.

BRIEF DESCRIPTION OF THE DRAWINGS

The accompanying drawings, which are incorporated in and constitute a part of this specification illustrate an embodiment of the invention and, together with the description, serve to explain the objects, advantages and principles of the invention.

In the drawings.

DETAILED DESCRIPTION OF THE PREFERRED EMBODIMENTS

Figure 1:
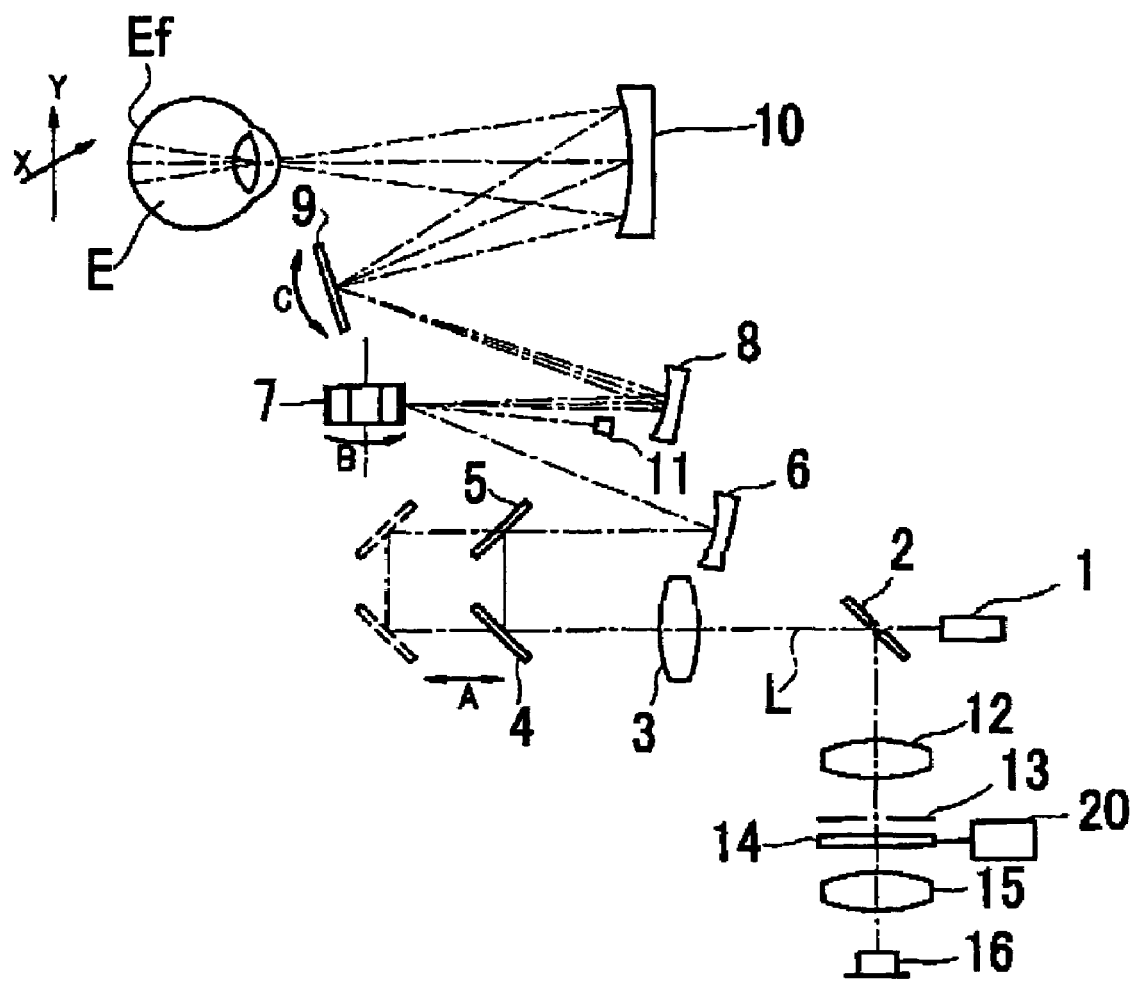
FIG. 1 is a schematic structural view of an optical system of a fundus observation apparatus in an embodiment of the present invention.

A detailed description of a preferred embodiment of the present invention will now be given referring to the accompanying drawings. FIG. 1 is a schematic structural view of an optical system of a fundus observation apparatus in the present embodiment.

A laser beam emitted from a laser source 1 is incident onto a polygon mirror 7a via a center opening of a perforated mirror 2, a lens 3, a plane reflecting mirror 4, a plane reflecting mirror 5, and a concave reflecting mirror 6. The beam reflected by the polygon mirror 7 is incident onto a galvano-mirror 9 via a concave reflecting mirror 8. The beam reflected by the galvano-mirror 9 is concentrated (condensed) on an observational objective part of a fundus Ef of an examinee's eye E via a concave reflecting mirror 10. The mirrors 4 and 5 are synchronously movable in a direction indicated by an arrow A to change an optical path length for focusing (diopter correction (movement)). The polygon mirror 7 is rotated in a direction indicated by an arrow B in order to scan the beam in a horizontal direction (an X-direction). The galvano-mirror 9 is swung (oscillated) in a direction indicated by an arrow C to scan the beam in a vertical direction (a Y-direction). With this structure, the beam is irradiated onto the objective part of the fundus Ef while scanning it in two dimensions (in the X- and Y-directions). These optical members constitute an irradiation optical system.

In the present embodiment, used as the laser source 1 is a semiconductor laser source which emits an infrared laser beam of linear polarized light having a predetermined polarization direction.

The beam reflected from the objective part of the fundus Ef travels back along the above mentioned irradiation optical system and is reflected by a portion surrounding the opening of the perforated mirror 2. The opening of the perforated mirror 2 is placed in a conjugate relation with the pupil of the eye E with respect to the lens 3. The beam reflected by the perforated mirror 2 comes into a focus at a center pinhole of a pinhole plate 13 through a lens 12. This pinhole is in a conjugate relation with the objective part of the fundus Ef with respect to the lens 12. The beam is then received by a photo-receiving element (a photo-detector) 16 through a polarizing member 14 and a lens 15. The polarizing member 14 is placed at a changeable angle with respect to a principal optical axis L of the beam (which passes through each center of the opening of the perforated mirror 2 and the pinhole of the pinhole plate 13). The polarizing member 14 is preferably disposed as close as possible to the photo-receiving element 16. These optical members constitute an observation optical system.

In the present embodiment, used as the photo-receiving element 16 is an Avalanche Photodiode (APD).

Figure 2:
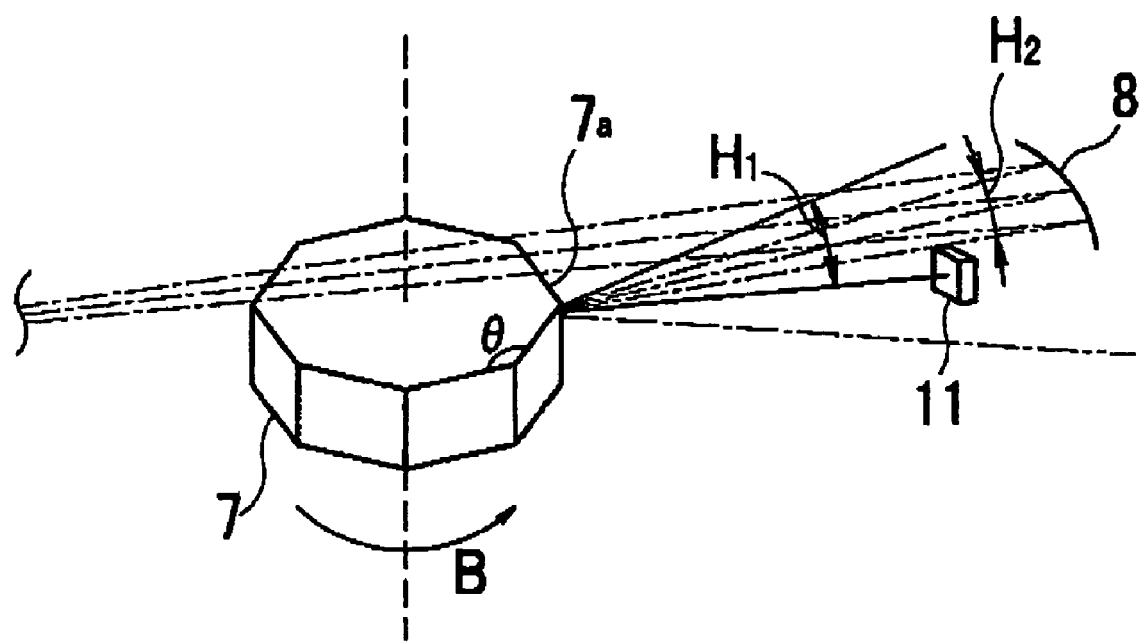
FIG. 2 is a schematic view showing placement of a sensor.

A photo-sensor 11 is disposed in a place that can receive the beam reflected by the polygon mirror 7. FIG. 2 is a schematic view showing the placement of the sensor 11. In the figure, a range H1 shown by thin lines indicates a scanning range of the beams by each reflecting surface 7a of the polygon mirror 7 and a range H2 shown by dashed lines indicates a scanning range of the beams to be used for image formation within the scanning range H1. The sensor 11 is placed in a position that receives the beam on or after entering in the scanning range H1 and before entering in the scanning range H2. The rotational speed of the polygon mirror 7 is constant and the position of the sensor 11 is fixed. Accordingly, the time needed for the beam received by the sensor 11 to enter in the scanning range H2 is uniform regardless of an angle θ between the reflecting surfaces 7a of the polygon mirror 7. Thus, the scanning range H2 can be set as a period from a first predetermined time T1 having elapsed since a detection time of the beam by the sensor 11 until a second predetermined time T2 having elapsed the same detection time, These elapsed times can be converted to rotation pulses of the polygon mirror 7. Only a signal representing that the beam is received within the scanning range H2 is used for image formation.

Figure 3:
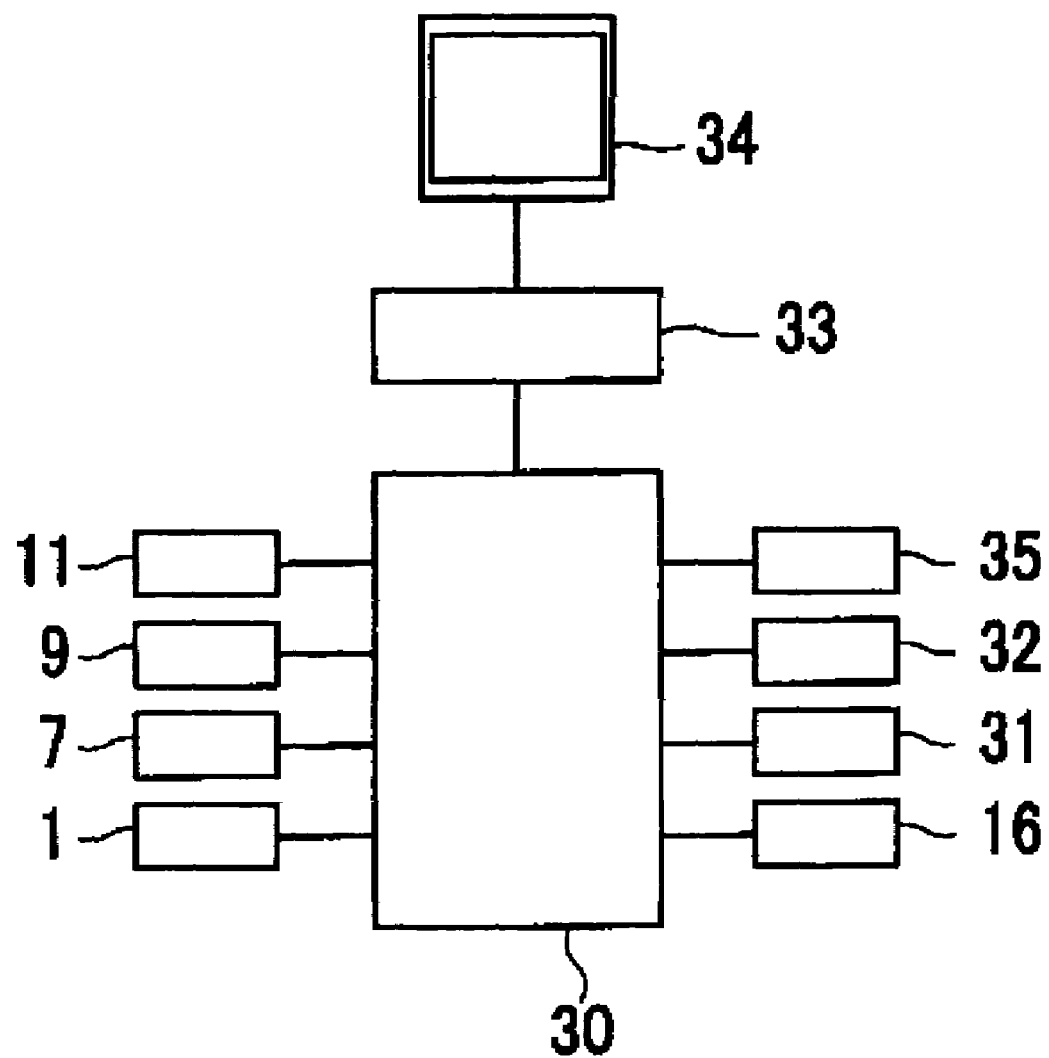
FIG. 3 is a schematic block diagram of a control system of the apparatus.

FIG. 3 is a schematic block diagram of a control system of the apparatus. Connected to a control part 30 which controls the entire apparatus are the laser source 1, the polygon mirror 7, the galvano-mirror 9, the sensor 11, the photo-receiving element 16, a moving part 31 for moving the mirrors 4 and 5, an input part 32 for inputting data on refractive power of the eye E in order to correct diopter, an image processing part 33 which forms an image based on the signal from the photo-receiving element 16, a memory part 35, and others. A monitor 34 displays the image formed by the image processing part 33.

Operations of the apparatus constructed as above will be described below.

An examiner inputs data on the refractive power of the eye E, which is a previously measured result through an eye refractive power measurement apparatus or the like, with the input part 32. The control part 30 stores the inputted refractive power data in the memory part 35 and causes the moving part 31 to move the mirrors 4 and 5 based on the data, thus correcting the diopter. The examiner then manipulates a joystick or the like not shown to move the apparatus after the diopter correction to make alignment with respect to the eye E so that the image of the objective part of the fundus Ef appears on the monitor 34.

The apparatus is arranged so that the objective part of the fundus Ef is in a conjugate relation with the pinhole of the pinhole plate 13. Accordingly, only the beam reflected by the objective part is allowed to pass through the pinhole and is received by the photo-receiving element 16. However, the light amount of the beam reflected by the objective part is small. If noise light (scattered light) besides the reflected beam is also allowed to pass through the pinhole and received by the photo-receiving element, the objective part image would be hard to observe. In this case, the arrangement angle of the polarizing member 14 has to be changed with respect to the optical axis L with the use of an operating member 20 to change the polarization direction of linear polarized light to be transmitted through the polarizing member 14.

Ganglion cells and others forming the retina of the fundus are anisotropic materials. On the retina, therefore, the beam reflected by the fundus slightly changes the polarization direction of linear polarized light depending on a fundus shape, a disease condition, etc. which differ from one examinee to another. While observing the image of the objective part displayed on the monitor 34, the examiner has to adjust the arrangement angle of the polarizing member 14 so that the objective part image appears most clearly.

Cells and molecules have a property of reflecting light when they are subjected to light. The changing states of polarization and wavelength of the reflected light vary according to a reflecting material (also according to solidity and shape thereof). Contained in the fundus are cells and molecules having self-fulorescence such as photoreceptor cells or lipofuscin molecules. To observe a desired objective part in detail, therefore the polarizing member 14 has to be adjusted to correspond the state of reflected light by a material contained in the objective part. Specifically, while observing the fundus, the examiner changes the arrangement angle of the polarizing member 14, so that capillary vessels can be viewed clearly.

In the present embodiment, the polarizing member 14 which transmits only the linear polarized light having a predetermined polarization direction is disposed between the pinhole 13 and the photo-receiving element 16, but it is not limited thereto. There may be adopted another structure capable of causing the photo-receiving element 16 to receive only a predetermined polarized light component and changing the polarized light component to be received. For example, 14 wave members may be placed on a laser source 1 side and a photo-receiving element 16 side respectively. In the present embodiment, further, the arrangement angle of the polarizing member 14 is manually changed. Alternatively, it may be electrically changed by operation of the input part 32 or the like. The present invention may also be applied to an apparatus for observing an anterior segment and others as well as the fundus observation apparatus.

While the presently preferred embodiment of the present invention has been shown and described, it is to be understood that this disclosure is for the purpose of illustration and that various changes and modifications may be made without departing from the scope of the invention as set forth in the appended claims.

What is claimed is:

1. An apparatus for observing an eye of an examinee, comprising:
    an irradiation optical system for irradiating and two-dimensionally scanning a laser beam onto an observational objective part of the eye;
    an observation optical system having a photo-receiving element, for photo-receiving the laser beam reflected by the objective part to obtain an image of the objective part, the observation optical system sharing at least a part of the irradiation optical system;
    a display which displays the obtained image;
    a polarizing member arranged on an optical axis of the observation optical system, an arrangement angle of the polarizing member with respect to the optical axis being changeable to change a polarized component to be transmitted by the polarizing member.

2. The apparatus according to claim 1, wherein
    the observation optical system includes a pinhole placed in a conjugate relation with the objective part, and
    the polarizing member is placed between the pinhole and the photo-receiving element.

3. The apparatus according to claim 1, wherein
    the irradiation optical system includes a laser source which emits an infrared laser beam of linear polarized light having a predetermined polarization direction, and
    the polarizing member is placed to transmit the beam reflected by the objective part.

* * * * *